United States Patent [19]
Agee et al.

[11] Patent Number: 6,063,087
[45] Date of Patent: May 16, 2000

[54] METHOD AND APPARATUS FOR INCREASING THE RANGE OF MOTION OF FINGERS SUFFERING FROM A LIMITED RANGE OF MOTION, THROUGH AN EXTERNAL FORCE TRANSMITTED TO THE SKELETON

[75] Inventors: John M. Agee, Cameron Park; Jeffrey Woodhouse, Sacramento; Francis C. King, Carmichael, all of Calif.

[73] Assignee: John M. Agee, Sacramento, Calif.; Trustee of The John M. Agee Trust dated August 15, 1996

[21] Appl. No.: 08/935,833

[22] Filed: Sep. 23, 1997

Related U.S. Application Data
[60] Provisional application No. 60/026,956, Sep. 23, 1996.

[51] Int. Cl.[7] .................................................. A61B 17/56
[52] U.S. Cl. ............................................ 606/55; 602/21
[58] Field of Search .................... 606/54–59; 602/20–22, 602/64

[56] References Cited

U.S. PATENT DOCUMENTS

| | | | |
|---|---|---|---|
| 4,602,620 | 7/1986 | Marx | 602/21 |
| 4,949,711 | 8/1990 | Gyovai et al. | 602/21 |
| 5,100,403 | 3/1992 | Hotchkiss et al. | |
| 5,102,411 | 4/1992 | Hotchkiss et al. | |
| 5,372,597 | 12/1994 | Hotchkiss et al. | |
| 5,376,091 | 12/1994 | Hotchkiss et al. | |

OTHER PUBLICATIONS

1999 Hand Therapy Catalog (selected pages) (North Coast Medical Inc., Morgan Hill, CA USA 95037–2845).
An Innovation IN PIP Fixation, BioSymMetRic Proximal Interphalangeal Joint Fixator (Biomet, Inc. advertisement).
The Continuous Elongation Treatment by the TEC Device for Severe Dupuytren's Contracture of the Fingers, Antonino Messina, M.D., and Jane Messina, M.D. (Turin, Italy).
Unstable Fracture Discloations of the Proximal Interphalangeal Joint, Treatment with the Force Cople Splint, John M. Agee, M.D.

*Primary Examiner*—Michael Buiz
*Assistant Examiner*—Julian W. Woo
*Attorney, Agent, or Firm*—Morrison & Foerster, LLP

[57] ABSTRACT

A wrist brace provides a mounting point, a means to hold the hand in position relative to the apparatus, and spreads the force evenly over a large area. Positioned over the dorsal surface of the brace is a "U" shaped transverse member that is attached to the wrist brace through two swivel joints on the ulnar and radial sides of the brace. The pivot means are positioned such that a straight line drawn between them generally passes through the axes of rotation of the metacarpal phalangeal (MP) joints. Positioned dorsally above the proximal interphalangeal (PIP) joint are two members, one of which has an arc shaped tail for its dorsal surface. The other is a slider block which engages and slides around this first arc member. The arc member is mounted to the middle phalanx of the subject finger in such a way that the projected center of the arc would be coincident with the axis of rotation of the PIP Joint. Two 'K' wires, fixation pins or screws are drilled through the dorsal cortex of the surface of the middle phalanx and extend into the palmar cortex. An adjustment means is provided to facilitate positioning the center of the arc coincident with the axis of rotation of the PIP joint. A linkage connects the slider block to the "U" shaped transverse member. The proximal end of this linkage is attached to the "U" shaped transverse member through another swivel joint. The distal end is attached to the slider block through a pin axis joint. This linkage allows the finger to deviate in the radial and ulnar direction and to rotate through its normal range of motion during finger extension and flexion. An adjustment means is added to the length of this linkage to permit the apparatus to accommodate different hand sizes.

65 Claims, 3 Drawing Sheets

METHOD AND APPARATUS FOR INCREASING THE RANGE OF MOTION OF FINGERS SUFFERING FROM A LIMITED RANGE OF MOTION, THROUGH AN EXTERNAL FORCE TRANSMITTED TO THE SKELETON

RELATED APPLICATIONS

This application claims the benefit of U.S. Provisional Application No. 60/026,956, filed Sep. 23, 1996, and entitled "METHOD AND APPARATUS FOR INCREASING THE RANGE OF MOTION OF FINGERS SUFFERING FROM A LIMITED RANGE OF MOTION, THROUGH AN EXTERNAL FORCE TRANSMITTED TO THE SKELETON".

BACKGROUND OF THE INVENTION

1. Technical Field

The present invention relates to a medical and surgical method and apparatus for the correction of injuries and disorders of the musculoskeletal system in general and contractures of joints in particular. More particularly this invention relates to a dynamic orthopedic device designed to increase the range of motion of joints suffering from contractures particularly the small joints of the hand.

2. Related Art

Skeletal joint contractures often result from trauma, including fractures and dislocations of joints. In addition, burns and their scar contracture reduce the range of motion of joints. Contractures also result from muscle imbalance across joints secondary to diseases such as leprosy. Dupuytren's disease commonly causes flexion contractures of the small joints of the hand. However, contractures can be flexion or extension contractures and can occur in any skeletal joint.

Traditionally, these injuries have been treated with various different modalities including splinting, serial plaster casts, and surgical release. Recently, significant innovations have resulted in more effective dynamic methods of treating such injuries in certain joints. For example, U.S. Pat. No. 5,376,091 to Hotchkiss et al., incorporated herein by reference, describes a dynamic finger joint support that has a proven clinical record of successful treatment of contractures. The Hotchkiss device is designed to allow, for example, the proximal interphalangeal (PIP) joint to be flexed and extended by a continuous passive motion machine that applies torque to the joint. Such flexion and extension is known to help overcome joint contractures so that the patient is often able to regain the full range of motion in the affected joint.

A deficiency of some prior art devices, generally referred to as hand splints, is that the torque required to increase the range of motion of the joint, can only be applied to the joint through the skin overlying the skeletal segments extending from either side of the joint. In addition, the force required to increase the range of motion of a joint needs to be applied for a significant amount of time. If the force is transmitted to the skeleton indirectly through the skin, the force compromises the circulation of the skin causing it to become tender, red and inflamed. In severe cases, particularly those with compromised sensation, ulcers may develop. As shown in FIGS. 1 and 2, the Hotchkiss device 5 avoids this problem for the distal interphalangeal (DIP) joint 10 by applying force directly to both the middle phalanx 12 and the distal phalanx 14. From the top view provided by FIG. 2, it is clear that pins 16, 18, 20, 22 are embedded in the skeletal elements through the lateral surface of the middle 12 and distal 14 phalanges.

Despite the successful clinical record of devices like Hotchkiss', there is room for improvement in the field. Many of the prior art devices and methods have potential problems and significant limitations that restrict their use in many applications. In particular, as shown in FIG. 2, Hotchkiss type devices 5 are required to be mounted on the lateral surface of the bones that extend from the contracted joint 10.

The Hotchkiss type device does not appear to be useable on metacarpal phalageal (MP) joints. In the case of the proximal interphalangeal (PIP) joint 24, for example, a Hotchkiss type device 5 appears to be most useful for the second and fifth PIP joints. However, because other fingers of the hand, including the webbing, would interfere with installation and use of the device on the third and fourth PIP joints, an alternate solution is required. Further, with regard to all of the PIP joints, there are soft tissues and tendons that glide along the lateral and medial surfaces of the phalanges, particularly the proximal phalanges of the fingers, that can be impaled by pins inserted into the sides of these phalanges, as required in Hotchkiss type devices used on the PIP joints. Additionally, installation of a Hotchkiss type device on the second and third DIP joints 10 would require the fingers to remain partially spread throughout the treatment period.

In light of such prior devices, what is needed is a means for biasing contracted joints that can be used on many different joints. What is further needed is a device that is not restricted to use only where it can be mounted on the lateral surface of the bones extending from a contracted joint. It would further be beneficial to identify a way to apply force directly to the skeleton without detrimentally disrupting soft tissue and tendons on the lateral surface of the bones extending from the joint. Such a device would preferably permit simultaneous treatment of adjacent joints.

In splinting techniques used in hand surgery and hand therapy, if a splint uses a single elastic element that crosses more than one joint to treat contracture of one or both joints, it is impossible to balance the torques applied to each of the joints. Thus, what is needed is a means to simultaneously apply independently controlled torque to multiple contracted joints that are adjacent along an appendage.

SUMMARY OF THE INVENTION

The above and other deficiencies and problems with the prior art are addressed by the present invention of a multiple contracted joint biasing apparatus and method. In the invention, an apparatus crosses and selectively controls torque forces applied to each skeletal joint in axial series, specifically when a first joint is proximal or distal to another. When applied to the hand, a first adjustable joint biasing torque apparatus is surgically attached to the dorsal surface of the middle phalanx of a finger. This first adjustable joint biasing torque apparatus is linked to a second proximal adjustable biasing torque apparatus by a rigid linkage. The second proximal adjustable biasing torque apparatus is positioned relative to the flexion-extension axis of the proximal joint by a removable brace that extends from the forearm across the wrist to cradle the hand.

More generally, a first adjustably biased mechanical joint is positioned on the extension side of a first contracted skeletal joint. A distal member extends from the first mechanical joint and is surgically attached to the bone extending from the contracted skeletal joint. A rigid linkage extends from the first mechanical joint and is attached to a second adjustably biased mechanical joint. A proximal member extends from the second mechanical joint and is removably attached to the appendage that extends proximally from the second contracted skeletal joint.

The first adjustably biased mechanical joint is operable to rotate with the same degrees of freedom as a normal, non-contracted skeletal joint of the same type as the first contracted skeletal joint. The adjustable biasing torque is applied to the skeletal joint via the distal member in the rotational direction of the desired range of skeletal joint motion. The second mechanical joint is positioned on the exterior side of a second contracted skeletal joint which is adjacent along the appendage that extends from the first skeletal joint. The second mechanical joint is operable to rotate with the same degrees of freedom as a normal, non-contracted joint of the same type as the second contracted joint. As with the adjustable biasing torque applied to the first skeletal joint by the first mechanical joint, the adjustable biasing torque for the second mechanical joint is applied to the second skeletal joint via the proximal member in the rotational direction of the desired range of motion for the second skeletal joint.

The adjustably biased mechanical joints of the apparatus are positioned so that they do not interfere with full extension of the patient's skeletal joints. They are held in place by the attachments to the patient such that their respective biasing torques are independent of each other and their center of rotation is coincident with the center of rotation of their associated skeletal joints.

The invention as applied to the second through fifth MP and PIP joints of the hand includes a wrist brace provided as a mounting point, as a means to hold the hand in position relative to the apparatus, and as a means to distribute the corrective force over a large area. A "U" shaped transverse member is positioned over the dorsal surface of the brace and is pivotally attached to the distal end on the ulnar and radial sides of the brace. The ends of the "U" shaped transverse member are positioned such that a transverse line between them generally passes through the axes of rotation of the MP joints.

Positioned dorsally above the PIP joint is an adjustably biased mechanical PIP joint. The mechanical PIP joint includes two members. The first member is an arcuate track that has an arc shaped track on its dorsal surface. The other is a slider block which engages and slides along the arcuate track member. The arcuate track member is mounted to the middle phalanx of the subject finger in such a way that the projected center of the arc is coincident with the axis of rotation of the PIP Joint. Two fixation pins are drilled into the dorsal surface of the middle phalanx and the arcuate track member is secured to these pins. An adjustment means is provided to facilitate positioning the center point of the arc coincident with the axis of rotation of the PIP joint.

A linkage rigidly connects the slider block to the "U" shaped transverse member. The proximal end of this linkage is attached to the "U" shaped transverse member through another swivel joint. The distal end of the linkage is attached to the slider block through a pin axis joint. The linkage allows the finger to deviate in the radial and ulnar direction and to rotate through its normal range of motion during finger extension and flexion. An adjustment means is added to the length of this linkage to permit the apparatus to accommodate different hand sizes.

Thus, important aspects of the invention include a method and apparatus for applying torques to adjacent contracted joints along an appendage for the purpose of manipulating the joints to increase their range of motion. The invention incorporates the following principals:

(a) The axis of rotation of the applied torque is coincident with the axis of rotation of the joint on which the torque is acting;

(b) The size and direction of the torque applied to adjacent joints along an appendage can be controlled independently;

(c) The torque is applied to the joint through a structure mounted directly to the skeleton;

(d) The magnitude and direction of the torques applied to laterally neighboring joints, for example, joints of adjacent fingers on the same hand, can be controlled independently;

(e) The force required to leverage or counteract the torque to the most proximal joint is applied to a brace like structure that distributes the force over a large surface of the appendage.

An embodiment of the invention for the MP and PIP joints includes a means to allow the finger to deviate in the radial and ulnar direction and to rotate through its normal range of motion during finger extension and flexion. This is achieved by connecting the part of the apparatus that is fixed to the middle phalanx of the finger to the remainder of the apparatus using a rigid linkage. The rigid linkage allows the part of the apparatus connected to the finger to move with the finger and to not restrict the movement of the finger in all of the normal planes of motion including that of MP flexion and extension where control is required.

The apparatus for this embodiment of the invention includes a force generating member such as a torsion spring, elastic band, coil compression or extension spring or the like; an apparatus that has a rotational movement where the axis of rotation of the device can be placed coincident with the axis of rotation of a particular finger joint; and a means for attaching the force generating member to the apparatus that has a rotational movement such that the force is converted into a torque that acts about the center of rotation of the rotational apparatus.

Without the force generating members attached, the skeletal joints remain free to flex or extend. If a force generating member is attached to only one of the mechanical joints of the apparatus, the other mechanical joint of the apparatus remains free to flex or extend. Thus, the mechanical joints of the apparatus are truly independent of each other and the torque generated by one mechanical joint of the apparatus is truly independent of any torque produced by the other.

BRIEF DESCRIPTION OF THE DRAWINGS

The features and advantages of the present invention will be understood upon consideration of the following detailed description of the invention in light of the accompanying drawings of which.

DETAILED DESCRIPTION OF THE PREFERRED EMBODIMENTS

The principles of the present invention are applicable to rehabilitate any set of contracted joints that are adjacent along a given appendage. For example, the present invention can be applied to simultaneously provide independent biasing torques to the PIP and MP joints. In addition, the present invention can be used to independently and simultaneously bias any combination of the joints in the first through fifth fingers. As a specific example of a preferred embodiment, the present invention is described herein as it would be applied to provide simultaneous yet independent biasing torques to the third (ring) finger PIP and MP joints of the left hand. However, the present invention may be adapted to accommodate other jointed appendages of the body, such as the foot for example.

Figure 1:
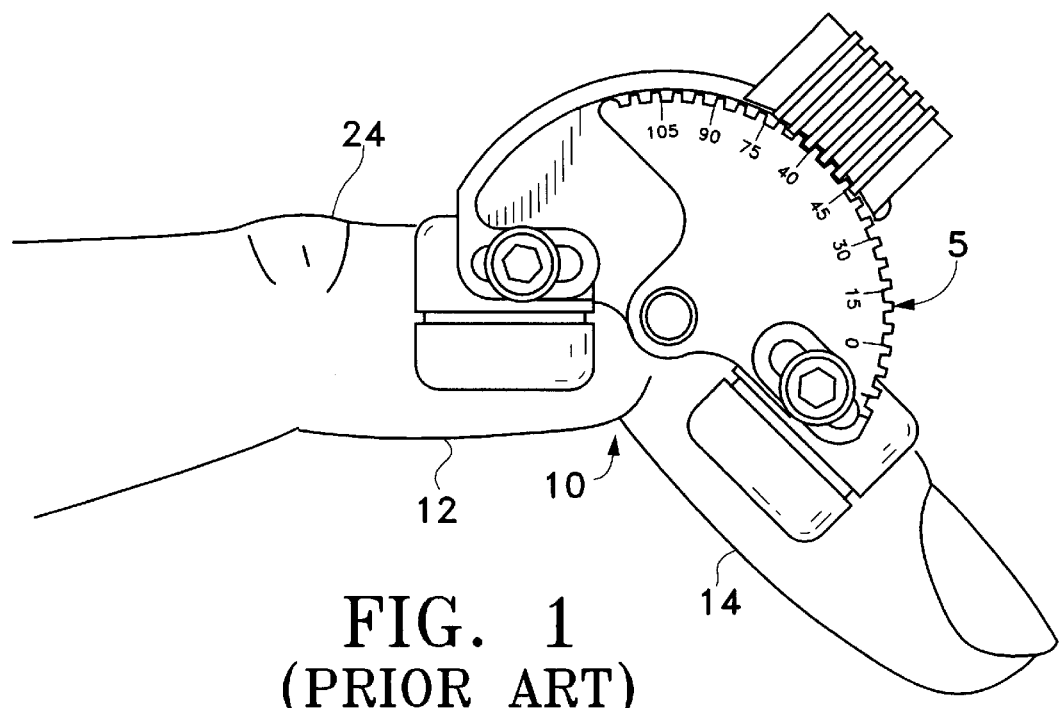
FIG. 1 is a side view depicting a dynamic DIP joint support of the prior art.
Figure 2:
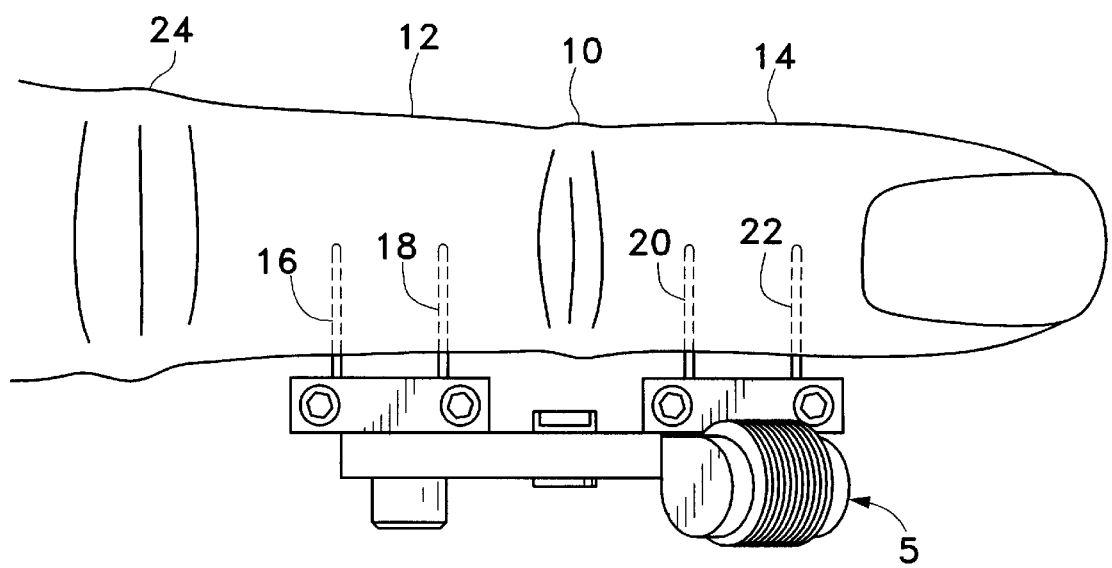
FIG. 2 is a top view depicting a dynamic DIP joint support of the prior art.
Figure 3:
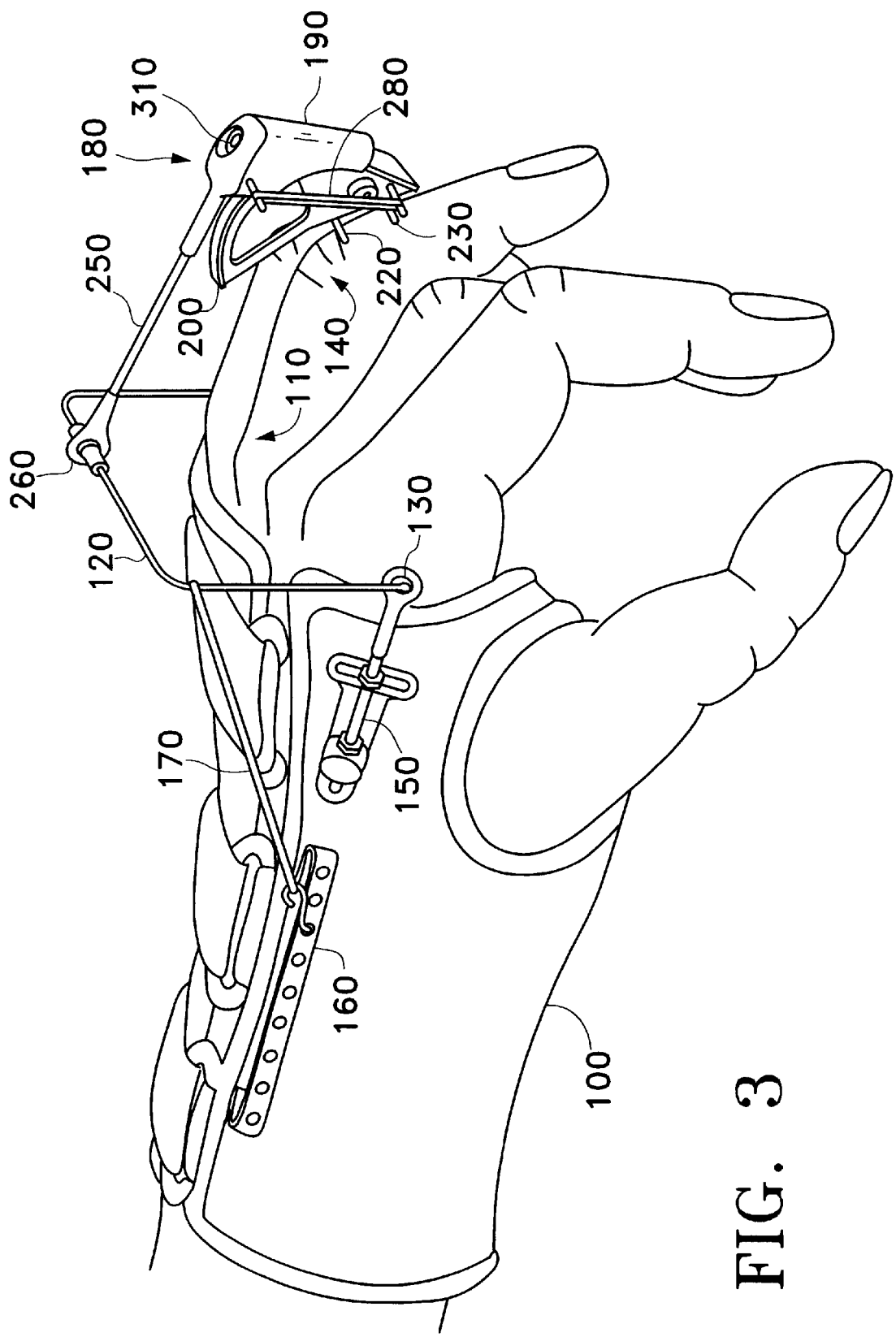
FIG. 3 is a perspective view depicting an embodiment of the present invention for the MP and PIP joints.

An exemplary embodiment of the invention is depicted in FIG. 3. A wrist brace 100 serves as a preferred means of attaching the proximal end of the apparatus to the patient. A commercially available brace such as model number 317085 available from Royce Medical Products of Camarillo, Calif. can be modified to include mounting points for the apparatus. The use of a wrist brace 100 provides the benefit of holding the hand in a desired position relative to the apparatus and it allows the biasing torque that is applied to the third MP joint 110 to be distributed over a large area. This avoids blanching of the skin when the torque is applied. Alternatively, a pair of pins surgically embedded in the third or other suitable metacarpal bone could be used to support the apparatus at the proximal end if necessary. This alternative would be required for example, in order to apply the invention to the first (thumb) MP and IP joints.

Positioned over the dorsal surface of the wrist brace 100 is a "U" shaped transverse member 120 that is attached to the wrist brace 100 through two swivel joints 130 on the ulnar and radial sides of the wrist brace 100. The swivel joints 130 are positioned such that a line drawn between their centers would generally pass through the axes of rotation of the MP joints of the hand. The "U" shaped transverse member 120 is a formed piece of wire of suitable diameter and strength to maintain its shape. In an alternative embodiment, the "U" shaped transverse member 120 can include extensions (not pictured) that extend in a palmar direction beyond the swivel joints 130. Such extensions would provide alternative locations for attaching a tension element 170 to apply a torque to the MP joint in the flexion direction.

In the example embodiment of the invention depicted in FIG. 3, the swivel joints 130 are ball and socket joints and are adjustably attached to the wrist brace 100 to facilitate lining up the swivel joints 130 with the axes of the MP joints. As shown in FIG. 3, the ball and socket joints (or any other suitable pivot means) include an extension 150 that allows the center of the joint to be located adjacent to the MP joints. The extension 150 can include a length adjustment or alternatively, VELCRO can be used to attach the swivel joints 130 to the wrist brace 100 at the desired location. The wrist brace 100 also includes an adjustable tension mount 160 for attaching a tension element 170 between the wrist brace 100 and the "U" shaped transverse member 120.

Positioned dorsally above the third PIP joint 140 is a mechanical PIP assist joint 180. The mechanical PIP assist joint 180 is comprised of two slidably engaged members: a slider block 190 and an arcuate track member 200. The arcuate track member 200 includes an arc shaped track on its dorsal surface and is mounted on the middle phalanx of the subject finger in such a way that the projected center of the arc would be coincident with the axis of rotation of the PIP Joint. The slider block 190 engages and slides along the arcuate track member 200. The arc shaped track terminates with stop pins (not pictured) that prevent the slider block 190 from disengaging from the arcuate track member 200 at the ends.

Figure 4:
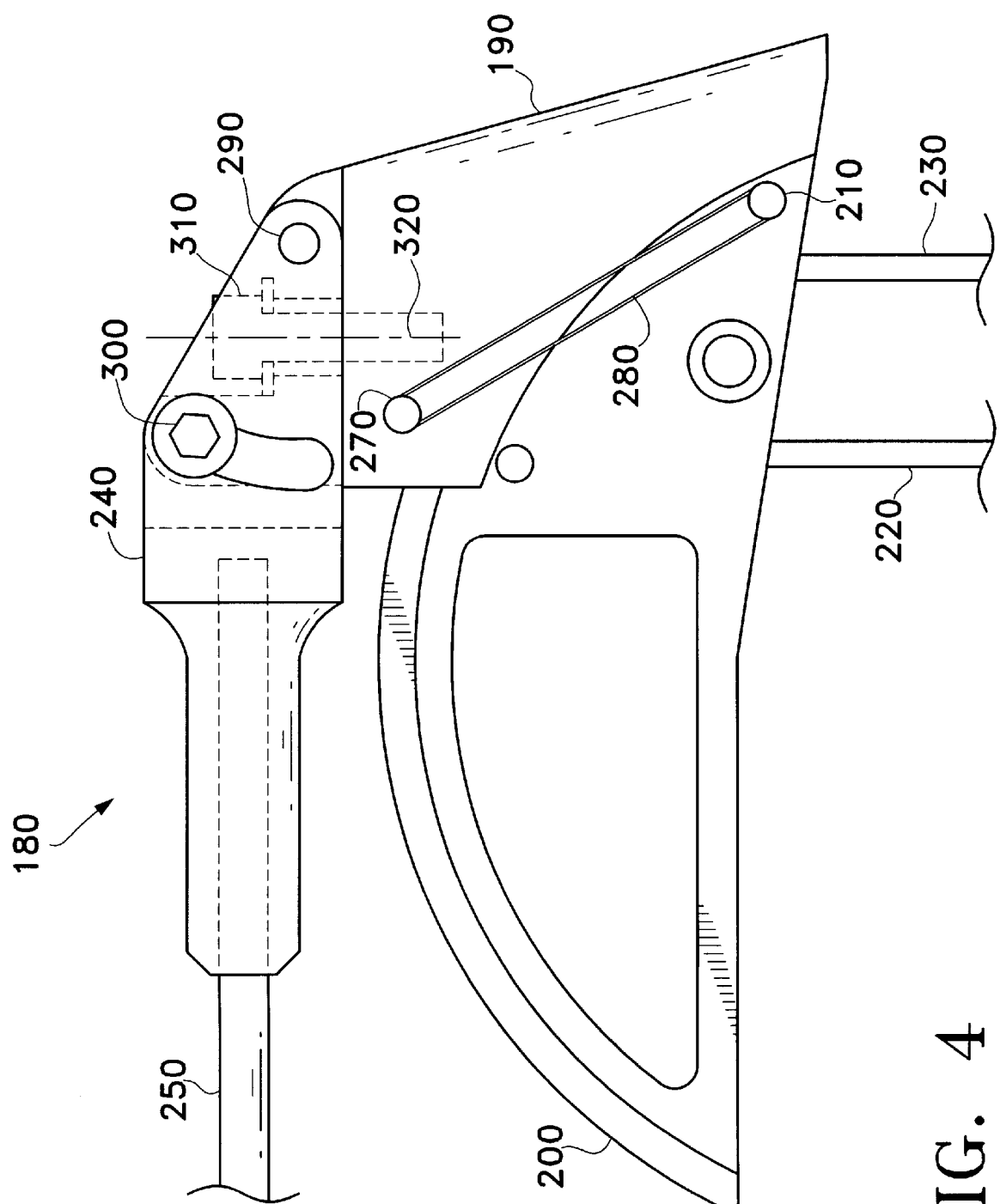
FIG. 4 is a side detail view of the PIP joint portion of the embodiment of the present invention depicted in FIG. 3.

Referring to FIG. 4, a detailed view of the mechanical PIP assist joint 180 is depicted. The angle of arc of the arcuate track member 200 is set based on the normal unimpaired range of the subject joint. In the case of the PIP joint 140, the preferred angle of the arc of the arcuate track member 200 is approximately 190 degrees. This angle supports a full range of motion for this joint without allowing the apparatus to impinge upon the finger. In the preferred embodiment of the invention, two 'K' wires, fixation pins, or screws 220, 230 extend from the arcuate track member 200 as shown in FIG. 4. These pins 220, 230 are surgically drilled through the dorsal cortex of the the middle phalanx and extend into the palmar cortex of the middle phalanx. The pins 220, 230 should not extend beyond the palmar cortex surface to avoid injury to the flexor tendons. The arcuate track member 200 is adjustably secured to these pins 220, 230. The adjustments are provided to facilitate positioning the center of the arc of the arcuate track member 200 coincident with the axis of rotation of the PIP joint.

An arc tension mounting pin 210 extends out from one of the lateral surfaces of the arcuate track member 200 and a corresponding slider tension mounting pin 270 extends out from one of the lateral surfaces of the slider block 190. In FIG. 4, the arc tension mounting pin 210 is located near the distal end of the arcuate track member 200. This allows the apparatus to exert an extension torque upon the PIP joint. Alternatively, the arc tension mounting pin 210 can be located on the lateral surface near the proximal end of the arcuate track member 200. This placement (not shown) of the arc tension mounting pin 210 would allow the mechanical PIP assist joint 180 to apply a flexion biasing torque to the PIP joint.

Referring back to FIG. 3, connecting the slider block 190 to the "U" shaped transverse member 120 is a rigid linkage 250. The proximal end of this rigid linkage 250 is attached to the "U" shaped transverse member 120 through a swivel joint 260. Referring back to FIG. 4, the distal end of the linkage 250 is attached to the slider block 190 through an adjustable linkage connector 240. The connector 240 is pivotally received on the upper surface of slider block 190. That is, connector 240 can rotate about bolt 310, which defines a pivot axis 320, relative to slider block 190. This linkage connector 240 includes an angle adjustment that allows the angle between the rigid linkage 250 and the slider block 190 to be adjusted to fit different sized hands. The angle adjustment can be comprised of a pin pivot hinge 290 and a locking set screw 300 or any functionally equivalent angle adjustment means.

Returning to FIG. 3, the swivel joint 260 coupling the linkage 250 to the "U" shaped transverse member 120 allows the subject finger to deviate in the radial and ulnar directions and to rotate through its normal range of motion during finger extension and flexion. Note that each increment of radial and ulnar deviation of the finger has an obligate degree of longitudinal rotation of the finger. Therefore, the linkage 250, with its pivot and swivel couplings, simultaneously permits rotation of the finger about its longitudinal axis, as well as the rotations of flexion and extension of the finger about its MP joint. An adjustment to the length of this rigid linkage 250 permits the invention to accommodate different hand sizes.

With this embodiment of the invention, both the PIP 140 and MP 110 joints are free to move through their full range of motion with no external force being applied. When the PIP joint 140 is flexed or extended the arcuate track member 200 is rotated around the axis of the joint and the slider block 190 travels along the arcuate track member 200. When the MP joint 110 is flexed or extended the arcuate track member 200 and the slider block 190 remain in the same position relative to each other. Motion of the MP joint 110 is transmitted through the arcuate track member 200 and slider block 190 via the linkage 250 to the "U" shape transverse member 120 which rotates on its swivel joints 130.

To treat a finger with a limited range of motion due to MP and/or PIP joint contractures, independent external forces can be applied to the skeleton using this embodiment of the invention such that the stiff joints will be subjected to a constant torque, which typically modifies the soft tissues of the joint, and thereby increases the range of motion in the desired direction. In the case of the PIP joint 140, the desired biasing torque is generated by a tension element 280 applied between the arcuate track member 200 and the slider block 190.

The tension element 280 (or "motor") can include tension springs (either extension or compression) or elastic bands, for example, and can be applied so that the torque applied to the contracted joint 140 will tend to increase the flexion or increase the extension of the subject joint 140. In the case of the MP joint 110, the tension element 170 is applied between the wrist brace 160 and the 'U' shaped transverse member 120. As with the PIP joint 140, an elastic band or either a compression or extension spring can be used to increase the flexion or extension of the MP joint 110. The amount of biasing torque applied to the joints can be controlled by changing the "strength" of the tension elements 170, 280. The biasing torque can also be changed by shifting the location of attachment of the tension element 170 on the 'U' shaped transverse member 120 such that it moves closer to pivot 130, thereby decreasing the leverage of the tension element 170 and therefore decreasing the extension torque on the MP joints of the fingers. In addition, the direction of the torque can be reversed by connecting the tension element 170 to the previously described palmar extensions of element 120, at a location palmar to pivot axis 130. The direction of the torque applied to the PIP joint can likewise be reversed by locating the mounting pin 210 (and its associated tension element 280) on the arcuate track 200 near the proximal end of the arcuate track 200.

In an alternative embodiment, the tension elements 170, 280 can be a rigid (non-elastic) adjustable length member. For example, a turnbuckle type device can be used to set a rigid tension element to any desired position. Another example of a rigid adjustable length member would include a worm screw driving mechanism with a releasable clutch, such as disclosed in the Hotchkiss patent, to set a desired length of the adjustable length member. This alternative embodiment would work to expand the joint's range of motion based on a stress/relaxation principle as opposed to the constant torque of the preferred embodiment. The rigid adjustable length member is set to torque against the joint's contracture for a period of time and once the joint relaxes, the length is reset to once again torque the joint. This resetting procedure is repeated until the full range of motion is restored to the joint.

In a situation where more than one finger on the same hand would benefit from an increased range of motion, additional arcuate track members 200 and slider blocks 190 could be attached to the additional fingers and connected to the "U" shaped transverse member 120. In this embodiment, the torque applied to each of the PIP joints can adjusted independently of each other. To allow the application of different biasing torques to the MP joints, additional "U" shaped transverse members within the existing "U" shaped transverse member 120 would be required. Alternatively, pins embedded in the metacarpal bones could be used to anchor the proximal end of the apparatus.

An essential feature of the invention is that the movement of the subject appendage is not restricted by the apparatus and the patient is not prevented from using the appendage during treatment. Further, in the embodiment described above, only two surgically installed pins are required to treat the PIP and MP joints.

In addition, the biasing torque generated and applied to each joint is independent of the torque generated and applied to the other joints. This allows treatment of the different joints with different biasing torques as required when treating multiple contracted joints. In other words, in the embodiment described above, moving either the PIP or MP joint through its complete range of motion has no functional effect on the other joint. This independent action results from the axes of rotation of the torque generating elements being coincident with their respective skeletal joint axes.

The foregoing description is considered to be for illustrative purposes only and in no way limiting to the invention. Many other modifications and alterations in the structure and method of operation of this invention will be apparent to those skilled in the art without departing from the scope and spirit of the invention. In particular, the invention can be used with adjacent joints along and appendage other than the example joints pictured. Additionally, other functionally equivalent materials and geometries can be substituted for those components described above.

What is claimed is:

1. An adjacent joint biasing apparatus comprising:
   first biasing means for biasing a first joint; and
   a second biasing means for biasing a second joint, said second biasing means coupled to said first biasing means,
   wherein the first and second joints are adjacent to each other along an appendage, said first biasing means including a first means for coupling to a distal segment of the appendage, said second biasing means including a second means for coupling to a proximal segment of the appendage, and said first and second biasing means are operative to bias their respective joints independently of each other.

2. The apparatus of claim 1, wherein said first and second biasing means rotatably move without substantially restricting the normal ranges of motion of their associated joints.

3. The apparatus of claim 1, wherein said first biasing means rotates about a first axis, said first biasing means being configured so that said first axis substantially coincides with an axis of rotation of the first joint.

4. The apparatus of claim 1, wherein said second biasing means rotates about a second axis, said second biasing means being configured so that said second axis substantially coincides with an axis of rotation of the second joint.

5. The biasing apparatus of claim 1 wherein said first means for coupling includes means for applying the biasing directly to a bone extending from the first joint.

6. The biasing apparatus of claim 1 wherein said second means for coupling includes means for applying the biasing to a segment of the appendage extending from the second joint.

7. The biasing apparatus of claim 1 wherein the first joint is a proximal interphalangeal joint joining a middle phalanx and a proximal phalanx, the second joint is a metacarpal phalangeal joint, said first means is couplable to the middle phalanx, and said second biasing means is coupled to a brace, said brace being positioned proximal to the second joint and being mechanically supportable by a forearm, wrist, and hand.

8. An adjacent joint biasing apparatus comprising:
a first mechanical assist joint for generating and applying a first biasing torque upon a first skeletal joint; and
a second mechanical assist joint for generating and applying a second biasing torque upon a second skeletal joint, said second mechanical assist joint coupled to said first biasing means,
wherein the first and second skeletal joints are adjacent to each other along an appendage, said first mechanical assist joint includes a first means for coupling to a middle phalanx, said second mechanical assist joint includes a second means for coupling to a brace, and said first and second mechanical assist joints are operative to generate and apply biasing torques upon their associated skeletal joints independently of each other.

9. The apparatus of claim 8, wherein said first and second mechanical assist joints rotatably move without substantially restricting the normal ranges of motion of their associated skeletal joints.

10. The apparatus of claim 8, wherein said first mechanical assist joint rotates about a first axis, said first mechanical assist joint being configured so that said first axis is substantially coincident with an axis of rotation the first skeletal joint.

11. The apparatus of claim 8, wherein said second mechanical assist joint rotates about a second axis, said second mechanical assist joint being configured so that said second axis is substantially coincident with an axis of rotation the second skeletal joint.

12. An apparatus, comprising:
a first rotatable mechanical joint configured to attach to a first contracted joint in an appendage, said first rotatable mechanical joint having a distal end configured to attach to a bone extending from the first contracted joint; and
a second rotatable mechanical joint connected to said first rotatable mechanical joint, said second rotatable mechanical joint having a proximal end configured to attach to an appendage joint extending proximally from a second contracted joint, the second contracted joint being adjacent to the first contracted joint,
wherein said first rotatable mechanical joint has a first axis of rotation, said first rotatable mechanical joint being configured so that said first axis of rotation substantially coincides with an axis of rotation of the first contracted joint,
wherein said second rotatable mechanical joint has a second axis of rotation, said second rotatable mechanical joint being configured so that said second axis of rotation substantially coincides with an axis of rotation of the second contracted joint,
wherein said first and second axes of rotation are independent, and
wherein said first and second mechanical joints are operable to apply torques independently to the first and second contracted joints, respectively.

13. The apparatus of claim 2, wherein the first joint is the proximal interphalangeal joint of the finger, wherein the second joint is the metacarpophalangeal joint of the finger,
wherein said first biasing means is configured to allow the finger to displace in the radial and ulnar directions and simultaneously to allow the first joint substantially to rotate through its normal range of motion during flexion and extension of the first joint,
and wherein said second biasing means is configured to allow the finger to deviate side to side and simultaneously allow an obligate longitudinal rotation which accompanies deviation of the finger, and simultaneously to allow the second joint to rotate through its normal range of motion during flexion and extension of the second joint.

14. The apparatus of claim 9, wherein the first skeletal joint is the proximal interphalangeal joint of the finger, wherein the second skeletal joint is the metacarpophalangeal joint of the finger,
wherein said first mechanical assist joint is configured to allow the finger to displace in the radial and ulnar directions and simultaneously to allow the first skeletal joint to rotate through its normal range of motion during flexion and extension of the first skeletal joint,
and wherein said second mechanical assist joint is configured to allow the finger to deviate side to side and simultaneously to allow an obligate longitudinal rotation which accompanies deviation of the finger, and simultaneously to allow the second skeletal joint to rotate through its normal range of motion during flexion and extension of the second skeletal joint.

15. The apparatus of claim 12, wherein the first contracted joint is the proximal interphalangeal joint of the finger, wherein the second contracted joint is the metacarpophalangeal joint of the finger,
wherein said first rotatable mechanical joint is configured to allow the finger to displace in the radial and ulnar directions and simultaneously to allow the first contracted joint to rotate through its normal range of motion during flexion and extension of the first contracted joint,
and wherein said second rotatable mechanical joint is configured to allow the finger to deviate side to side and simultaneously to allow an obligate longitudinal rotation which accompanies deviation of the finger, and simultaneously to allow the second contracted joint to rotate through its normal range of motion during flexion and extension of the second contracted joint.

16. An apparatus for biasing a joint of a human upper extremity, the upper extremity having skin, a skeletal structure, and at least one finger with a dorsal aspect and at least one extremity joint, comprising:
a. a distal attachment portion having a distal attachment interface;
b. a frame; and
c. a proximal attachment portion;
wherein said distal attachment portion is configured to affix to a distal attachment site on the dorsal aspect of a finger at said distal attachment interface, said proximal attachment portion is configured to attach to a portion of the extremity proximal to the distal attachment site, and said frame is rotatable with respect to both said distal attachment portion and said proximal attachment portion.

17. The apparatus of claim 16, wherein said distal attachment portion is configured to attach to the skeletal structure of said upper extremity using a pin or screw.

18. The apparatus of claim 16, wherein said distal attachment portion is configured to attach to the dorsal aspect of the middle phalanx bone of the extremity.

19. The apparatus of claim 16, wherein said proximal attachment portion is a brace, said brace being configured to attach to the extremity and transmit loads thereto through a relatively large surface area of said skin.

20. The apparatus of claim 16, wherein said proximal attachment portion comprises a proximal bony attachment element, said proximal bony attachment element being configured to attach rigidly to a bone of the extremity.

21. The apparatus of claim 20, wherein said bony attachment element is configured to attach to a metacarpal bone.

22. The apparatus of claim 20, wherein said proximal bony attachment element comprises an elongate metallic member.

23. The apparatus of claim 22, wherein said elongate metallic member is a screw having threads.

24. The apparatus of claim 22, wherein said elongate metallic member is a pin.

25. The apparatus of claim 16 further comprising a first biasing member, said first biasing member being removably attachable to both of said frame and said distal attachment portion and being configured to apply a first moment therebetween about a first moment axis.

26. The apparatus of claim 25, wherein said first moment axis is substantially coincident with an axis of rotation of a first proximal extremity joint, the first proximal extremity joint being positioned proximally in relation to said distal attachment interface.

27. The apparatus of claim 26, wherein said frame is rotatably interfaced with each of said proximal attachment portion and said distal attachment portion to prevent substantially transfer of said first moment to said proximal attachment portion and to allow for transfer of axial loads between said distal attachment portion and said proximal attachment portion.

28. The apparatus of claim 26, wherein said distal attachment portion and said frame are rotatably interfaced in a manner which allows for application of said first moment through a range of motion of the first proximal extremity joint.

29. The apparatus of claim 28, wherein said range of motion is less than the normal physiologic range of motion for the first proximal extremity joint.

30. The apparatus of claim 28, wherein said range of motion is the normal physiologic range of motion for the first proximal extremity joint.

31. The apparatus of claim 26, wherein said first biasing member is configured to apply said first moment to cause the first proximal extremity joint to rotate in flexion.

32. The apparatus of claim 26, wherein said first biasing member is configured to apply said first moment to cause the first proximal extremity joint to rotate in extension.

33. The apparatus of claim 26, wherein the first proximal extremity joint is a proximal interphalangeal joint of a finger.

34. The apparatus of claim 33, wherein said frame is configured to allow said finger to displace in the radial and ulnar directions and simultaneously allow the first proximal extremity joint to rotate through a normal range of motion during flexion and extension of the first proximal extremity joint.

35. The apparatus of claim 33, wherein said frame is configured to allow said finger to displace in the radial and ulnar directions and simultaneously allow the first proximal extremity joint to rotate through a normal range of motion during flexion and extension of the first proximal extremity joint, and simultaneously allow the finger to deviate side to side and simultaneously enjoy an obligate longitudinal rotation which may accompany deviation of the finger, and simultaneously allow the metacarpophalangeal joint of said finger to rotate through its normal range of motion during flexion and extension of the metacarpophalangeal joint of said finger.

36. The apparatus of claim 26, wherein said frame is rotatably interfaced with each of said proximal attachment portion and said distal attachment portion to substantially prevent transfer of said first moment to extremity joints other than said proximal interphalangeal joint.

37. The apparatus of claim 16 further comprising a first biasing member, said first biasing member being removably attachable to both of said frame and said proximal attachment portion and being configured to apply a first moment therebetween about a first moment axis.

38. The apparatus of claim 37, wherein said first moment axis is substantially coincident with an axis of rotation of a first proximal extremity joint, the first proximal extremity joint being positioned proximally in relation to said distal attachment site.

39. The apparatus of claim 38, wherein said frame is rotatably interfaced with each of said proximal attachment portion and said distal attachment portion to substantially prevent transfer of said first moment to said distal attachment portion, and to allow for transfer of axial loads between said distal attachment portion and said proximal attachment portion.

40. The apparatus of claim 38, wherein said proximal attachment portion and said frame are rotatably interfaced in a manner which allows for application of said first moment through a range of motion of the first proximal extremity joint.

41. The apparatus of claim 40, wherein said range of motion is less than the normal physiologic range of motion for the first proximal extremity joint.

42. The apparatus of claim 40, wherein said range of motion is the normal physiologic range of motion for the first proximal extremity joint.

43. The apparatus of claim 38, wherein said first biasing member is configured to apply said first moment to cause the first proximal extremity joint to rotate in flexion.

44. The apparatus of claim 38, wherein said first biasing member is configured to apply said first moment to cause the first proximal extremity joint to rotate in extension.

45. The apparatus of claim 38, wherein the first proximal extremity joint is a metacarpophalangeal joint of a finger.

46. The apparatus of claim 45, wherein said frame is configured to allow said finger to displace in the radial and ulnar directions and simultaneously allow the proximal interphalangeal joint of said finger to rotate through a normal range of motion during flexion and extension of the proximal interphalangeal joint of said finger, simultaneously allow the finger to deviate side to side and simultaneously enjoy an obligate longitudinal rotation which may accompany deviation of the finger, and simultaneously allow the first proximal extremity joint to rotate through its normal range of motion during flexion and extension of the first proximal extremity joint.

47. The apparatus of claim 45, wherein said frame is rotatably interfaced with each of said proximal attachment portion and said distal attachment portion to substantially prevent transfer of said first moment to extremity joints located at substantially different locations along said extremity from said metacarpophalangeal joint.

48. The apparatus of claim 26, further comprising a second biasing member, said second biasing member being removably attachable to both said frame and said proximal attachment portion and being configured to apply a second moment therebetween about a second moment axis.

49. The apparatus of claim 48, wherein said second moment axis is substantially coincident with an axis of rotation of a second proximal extremity joint, the second proximal extremity joint being positioned proximally in relation to said distal attachment site, and being positioned at a different location along the extremity from the first proximal extremity joint.

50. The apparatus of claim 48, wherein said frame is configured to allow for substantially independent application of said second moment and said first moment.

51. The apparatus of claim 49, wherein said proximal attachment portion and said frame are rotatably interfaced to allow for application of said first moment through a range of motion of the second proximal extremity joint.

52. The apparatus of claim 49, wherein said range of motion is less than the normal physiologic range of motion for the second proximal extremity joint.

53. The apparatus of claim 49, wherein said range of motion is the normal physiologic range of motion for the second proximal extremity joint.

54. The apparatus of claim 49, wherein said second biasing member is configured to apply said second moment to cause the second proximal extremity joint to rotate in flexion.

55. The apparatus of claim 49, wherein said second biasing member is configured to apply said second moment to cause the second proximal extremity joint to rotate in extension.

56. The apparatus of claim 49, wherein the second proximal extremity joint is a metacarpophalangeal joint of a first finger and the first proximal extremity joint is a proximal interphalangeal joint of said first finger.

57. The apparatus of claim 56, wherein said frame is configured to allow said first finger to displace in the radial and ulnar directions and simultaneously allow the first proximal extremity joint to rotate through a normal range of motion during flexion and extension of the first proximal extremity joint.

58. The apparatus of claim 56, wherein said frame is configured to allow said first finger to displace in the radial and ulnar directions and simultaneously allow the first proximal extremity joint to rotate through a normal range of motion during flexion and extension of the first proximal extremity joint, and simultaneously allow the first finger to deviate side to side and simultaneously enjoy an obligate longitudinal rotation which may accompany deviation of the first finger.

59. The apparatus of claim 56, wherein said frame is configured to allow said first finger to displace in the radial and ulnar directions and simultaneously allow the first proximal extremity joint to rotate through a normal range of motion during flexion and extension of the first proximal extremity joint, simultaneously allow the first finger to deviate side to side and simultaneously enjoy an obligate longitudinal rotation which may accompany deviation of the first finger, and simultaneously allow the second proximal extremity joint to rotate through its normal range of motion during flexion and extension of the second proximal extremity joint.

60. A method of using the apparatus of claim 25 to bias a joint of the human upper extremity comprising affixing said distal attachment portion to the dorsal aspect of said finger at said distal attachment interface, attaching said proximal attachment portion to a portion of the extremity proximal to said distal attachment site, positioning said frame in rotatable attachment with said distal attachment portion and said proximal attachment portion, removably attaching said first biasing member to said frame and said distal attachment portion, and applying said first moment between said frame and said distal attachment portion about a first moment axis.

61. A method of using the apparatus of claim 50 independently to bias two joints of the human upper extremity comprising affixing said distal attachment portion to the dorsal aspect of said finger at said distal attachment interface, attaching said proximal attachment portion to a portion of the extremity proximal to said distal attachment site, positioning said frame in rotatable attachment with said distal attachment portion and said proximal attachment portion, removably attaching said first biasing member to said frame and said distal attachment portion, applying said first moment between said frame and said distal attachment portion about a first moment axis, removably attaching said second biasing member to said frame and said proximal attachment portion, and applying said second moment between said frame and said proximal attachment portion about a second moment axis.

62. A method of using the apparatus of claim 37 to bias a joint of the human upper extremity comprising affixing said distal attachment portion to the dorsal aspect of said finger at said distal attachment interface, attaching said proximal attachment portion to a portion of the extremity proximal to said distal attachment site, positioning said frame in rotatable attachment with said distal attachment portion and said proximal attachment portion, removably attaching said first biasing member to said frame and said proximal attachment portion, and applying said first moment between said frame and said proximal attachment portion about a first moment axis.

63. The apparatus of claim 16, wherein said frame is configured to allow said finger to displace in the radial and ulnar directions and simultaneously allow the joint immediately proximal of the distal attachment portion to rotate through a normal range of motion during flexion and extension of the joint immediately proximal of the distal attachment portion.

64. The apparatus of claim 16, wherein said frame is configured to allow said finger to displace in the radial and ulnar directions and simultaneously allow the joint immediately proximal of the distal attachment portion to rotate through a normal range of motion during flexion and extension of the joint immediately proximal of the distal attachment portion, and simultaneously allow the finger to deviate side to side and simultaneously enjoy an obligate longitudinal rotation which may accompany deviation of the finger.

65. The apparatus of claim 16, wherein said frame is configured to allow said finger to displace in the radial and ulnar directions and simultaneously allow the joint immediately proximal of the distal attachment portion to rotate through a normal range of motion during flexion and extension of the joint immediately proximal of the distal attachment portion, and simultaneously allow the finger to deviate side to side and simultaneously enjoy an obligate longitudinal rotation which may accompany deviation of the finger, and simultaneously allow the joint immediately proximal to the joint which is immediately proximal to the distal attachment portion to rotate through its normal range of motion during flexion and extension of the joint immediately proximal to the joint which is immediately proximal to the distal attachment portion.

* * * * *